United States Patent
Yue et al.

(10) Patent No.: US 8,653,261 B2
(45) Date of Patent: Feb. 18, 2014

(54) MODIFIED ACTINOMYCIN-BASED NUCLEIC ACID STAINS AND METHODS OF THEIR USE

(75) Inventors: Stephen Yue, Eugene, OR (US); Jixiang Liu, Eugene, OR (US); Jolene Bradford, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 155 days.

(21) Appl. No.: 13/126,150

(22) PCT Filed: Oct. 26, 2009

(86) PCT No.: PCT/US2009/062012
§ 371 (c)(1),
(2), (4) Date: May 27, 2011

(87) PCT Pub. No.: WO2010/062536
PCT Pub. Date: Jun. 3, 2010

(65) Prior Publication Data
US 2011/0236887 A1 Sep. 29, 2011

Related U.S. Application Data

(60) Provisional application No. 61/108,736, filed on Oct. 27, 2008.

(51) Int. Cl.
*C07D 265/38* (2006.01)

(52) U.S. Cl.
USPC .......................................... 544/102; 544/103

(58) Field of Classification Search
USPC ....................................................... 544/102
See application file for complete search history.

(56) References Cited

FOREIGN PATENT DOCUMENTS

| WO | WO-2010/062536    | 6/2010 |
| WO | WO-2010/062536 A3 | 8/2010 |

OTHER PUBLICATIONS

U.S. Appl. No. 61/108,736, Yue, Stephen et al.
Graves, D. E., et al., "7-azidoactinomycin D: A Novel Probe for Examining Actino mycin D-DNA Interactions", *Journal of Biological Chemistry*,264(1) 1989 , 7262-7266.
PCT/US2009/062012, "International Search Report and Written Opinion Received Mailed on Jun. 25, 2010".
Sengupta, S K., "7-SUbstituted Actinomycin D Analogs. Chemical and Growth-Inhibitory Studies", *Journal of Medicinal Chemistry* vol. 18, No. 12 Dec. 1975 , 1175-1180.
Zelenin, A. V., et al., "7-amino-actinomycin D as a specific fluorophore for DNA content analysis by laser flow cytometry", *Cytometry*,5(4) 1984 , 348-354.
Nikitin, S. M., et al., "DNA base pair sequence-specific ligands .V.Act inomycin D analogs substituted at position 7 of the phenoxazone chromophore", *Russian Journal of Bioorganic Chemistry*,7(4) 1981, 542-551.
Nikitin, S. M., et al., "DNA base pair specific ligands.IV. Act inomyc in D analogs: amide derivatives of act inocin with substituents in position 7", *Russian Journal of Bioorganic Chemistry*,6(5) formul as II I-VI . 1980, 743-751.
PCT/US09/62012, "International Preliminary Report on Patentability Mailed May 12, 2011".
Bailly, C. et al., "Use of a Photoactive Drivative of Actinomycin to Investigate Shuffling Between Binding Sites on DNA", *Biochemistry*, 1994, pp. 8736-8745.
EP09829560.3, "Supplementary Search Report", Mailed on Jul. 2, 2012, pp. 1-7.
Seela, F. , "Actinomin and 4,6-Didemethyl-di-tert-butyl-actinomine-Model Compounds for Studies of the Actinomycin-DNA Interaction", *Zeitschrift Fur Naturforschuntg*, vol. 26, 1971, pp. 875-878.
Sehgal, R. et al., "Synthesis and Biological Properties of Actinomycin D Chromophoric Analogues Substituted at the 7-Carbon with Aziridine and Aminopropoxy Functions", *J. Medicinal Chem.*, vol. 30(9), 1987, pp. 1626-1631.

*Primary Examiner* — Kahsay Habte
(74) *Attorney, Agent, or Firm* — Life Technologies Corporation

(57) ABSTRACT

Actinomysin-based near IR emitting compounds and methods of their use as nucleic acid stains are provided. The actinomysin-based near IR emitting compounds have the structure:

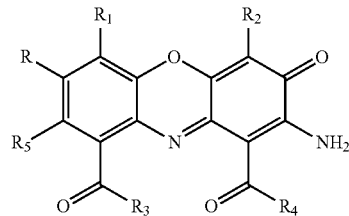

wherein R is H or $NH_2$; $R_1$, $R_2$, $R_3$, and $R_4$ are independently a moiety comprising 1-30 atoms selected from H, O, C, and N, wherein the atoms are in a linear, branched, or cyclic configuration; $R_3$ and/or $R_4$ comprise a quaternary nitrogen atom; and $R_5$ is H, F, or Cl.

8 Claims, 3 Drawing Sheets

MODIFIED ACTINOMYCIN-BASED NUCLEIC ACID STAINS AND METHODS OF THEIR USE

CROSS-REFERENCE TO RELATED APPLICATIONS

This application is a U.S. National Stage Application of PCT application no. PCT/US09/62012, filed Oct. 26, 2009, which claims priority to U.S. application No. 61/108,736, filed Oct. 27, 2008, which disclosures are herein incorporated by reference in their entirety.

FIELD OF THE INVENTION

The present application relates to actinomycin analogues and their use as nucleic acid stains (e.g., nucleic acid stains for dead cell identification or for DNA content cell cycle analysis).

BACKGROUND OF THE INVENTION

Fluorescent compounds can be used to directly stain or label a sample so that the sample can be identified and quantitated. Fluorescent dyes are widely used in biological applications in which a highly sensitive detection reagent is desirable. For example, fluorescent dyes may be added as part of an assay for a biological target analyte. Dyes that are able to preferentially bind to a specific biological component in a sample can be used to determine the presence or quantity of that specific ingredient.

Fluorescent dyes with longer wavelength absorption and emission are particularly useful in conjunction with materials of biological origin such as cells and tissues, where background or inherent fluorescence or absorption often interferes with detection of the added fluorescent dye. Furthermore, biological specimens often have decreasing levels of both absorption and fluorescence emission as the illumination energy approaches the infrared.

Certain fluorescent compounds have a strong affinity for DNA and can serve as a fluorescent marker for DNA. Fluorescent markers for DNA find use in various applications, including fluorescence microscopy and flow cytometry. A commonly used fluorescent compound that is known to have an affinity for double-stranded DNA is 7-aminoactinomycin D (7-AAD). 7-AAD can be efficiently excited using standard helium-neon and argon lasers, laser diodes or arc lamps or other such focused light sources (absorption maximum at 546 nm) and exhibits a large Stokes shift (emission maximum at 647 nm), which makes it compatible with many types of fluorophores and useful in multicolor applications. 7-AAD is widely used as a nuclear stain for dead cells, since it does not readily pass through intact cell membranes. In cell viability assays, cells with compromised membranes will stain with 7-AAD, while live cells with intact cell membranes will not. A limitation of using 7-AAD as a nuclear stain is that the staining process (i.e., the time required for 7-AAD to associate with the DNA) requires a relatively long incubation time. For example, for dead cell identification, the staining process typically takes about 30 minutes to fully equilibrate. Long incubation times hamper the use of 7-AAD in high throughput applications and other applications requiring rapid staining or analysis. Additionally, the DNA content cell cycle histogram generated using fixed cells stained with 7-AAD exhibits a high degree of variability, as measured by the % Coefficient of Variation (% CV) of the G0G1 peak of the histogram.

Thus, there exists a need for fluorescent compounds that selectively and rapidly stain cells with compromised cell membranes and have excitation spectra in the visible region and emission spectra in the near infrared (IR) region of the electromagnetic spectrum.

SUMMARY OF THE INVENTION

The present application relates to actinomycin-based near IR emitting compounds; kits containing the described compounds; and their use in fluorescence-based detection of biological materials or other materials containing or suspected of containing nucleic acids. The actinomycin-based compounds of the invention selectively and rapidly associate with nucleic acid molecules (e.g., nucleic acid molecules contained in cells). The subject compounds can readily enter cells having compromised cell membranes (e.g., dead cells). Rapid staining and permeation into cells shortens incubation times, thereby permitting the subject compounds to be used in applications requiring rapid staining and analysis of cells (e.g., high throughput screening). Further, the modified actinomycin compounds of the invention also demonstrate low variability in DNA content cell cycle analysis using fixed cells, as measured with the % CV of the G0G1 peak of the histogram.

The compounds of the invention exhibit very long wavelength emission bands upon excitation with light of an appropriate wavelength, which make them applicable for use in sample systems that possess transparency primarily in the near-infrared region, or where the use of near-infrared wavelengths is particularly advantageous. The compound dyes also are relatively stable to photobleaching, remaining intensely fluorescent even after repeated exposure to the intense illumination of an epifluorescence microscope.

In one aspect, a compound having the structure represented by Formula 1 is provided:

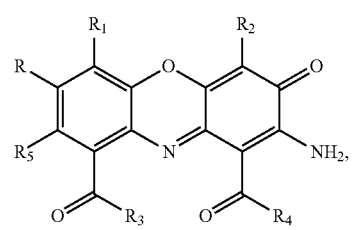

Formula 1 wherein R is H or $NH_2$; $R_1$, $R_2$, $R_3$, and $R_4$ are independently a moiety comprising 1-30 atoms selected from H, O, C, and N, wherein the atoms are in a linear, branched, or cyclic configuration; and $R_5$ is H, F, or Cl. Exemplary compounds of the invention are represented by the following chemical structures:

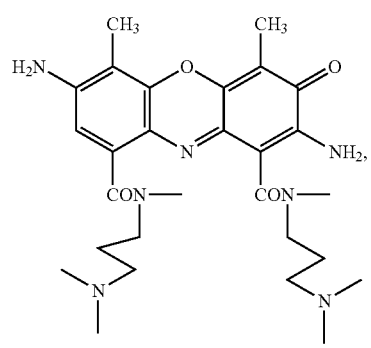

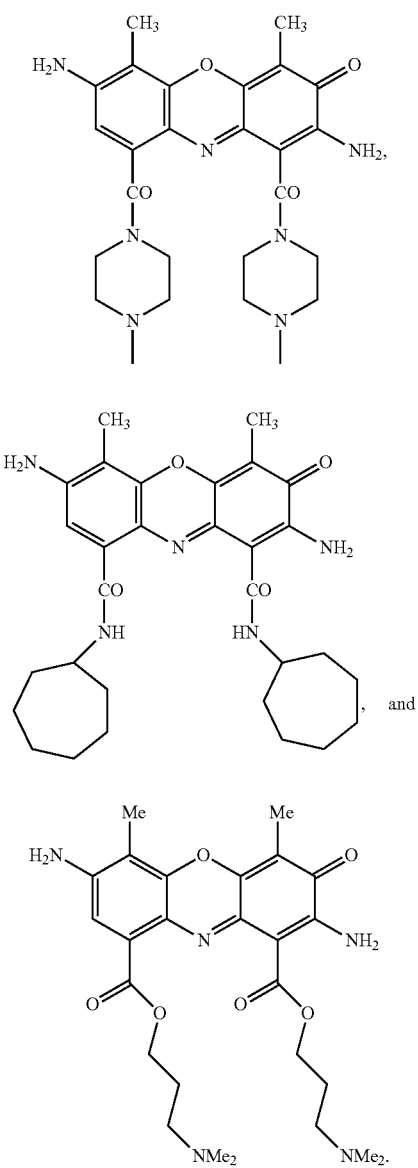
Other exemplary compounds of the invention can be represented by the following chemical structures:
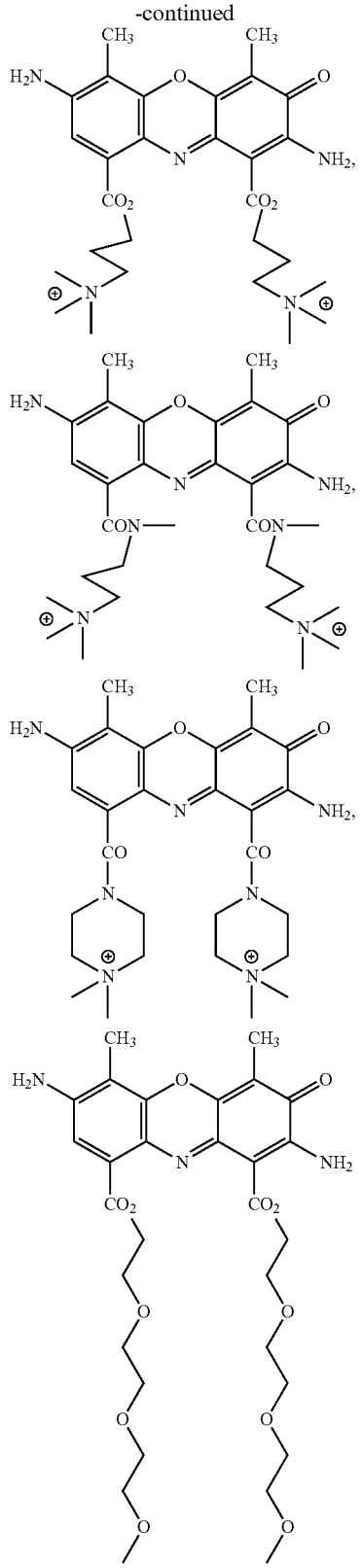
or a salt thereof.
In another aspect, a complex of an actinomycin-based compound and a nucleic acid molecule (e.g., double-stranded DNA (dsDNA)) is provided.

In yet another aspect, methods of using the actinomycin-based compounds of the invention are provided. The compounds of the invention can be used in numerous fluorescence-based cellular assays, including staining of nucleic acids within the cell, differentiating live and dead cells in a sample (e.g., via flow cytometry or imaging), measuring total DNA content, in cell cycle analysis assays, labeling particles labeled with nucleic acids, and labeling free nuclei. Also provided are methods for multiplexing the aforementioned assays with other fluorescent based or non-fluorescent based measurements.

In yet another aspect, kits for detecting nucleic acid in a sample are provided that include an actinomycin-based compound of the invention.

DETAILED DESCRIPTION OF THE INVENTION

Figure 1:
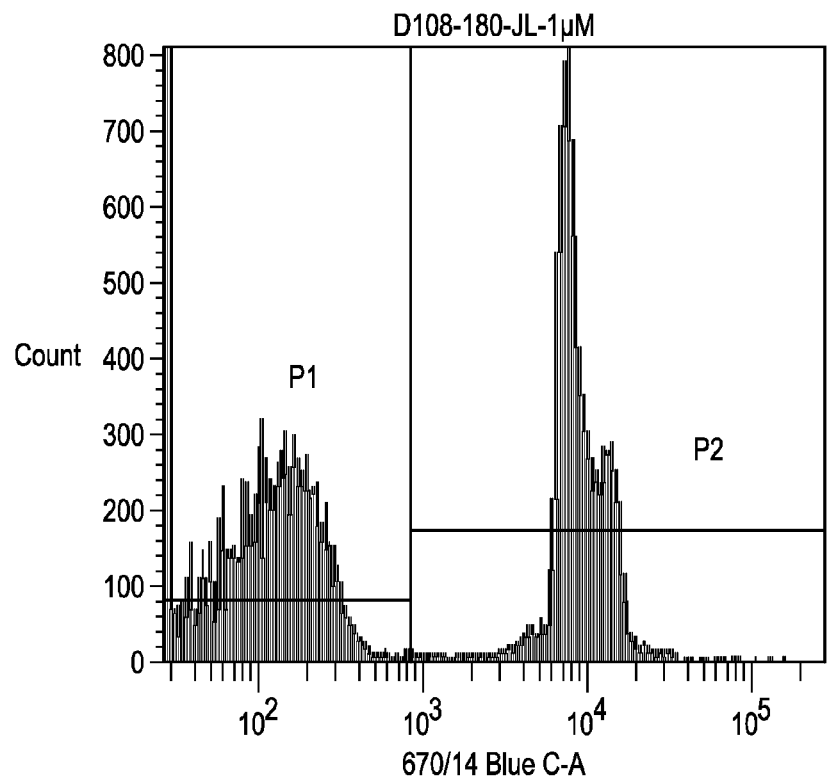
FIG. 1 is a flow cytometry plot for a mixture (50:50) of live and heat-killed Jurkat T lymphocytic leukemia cells treated with 1 µM Compound 7 and incubated for 5 minutes at room temperature. The live and dead cells are distinctly separated.

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. It also should be noted that the term "about", when used to describe a numerical value, shall encompass a range up to ±15% of that numerical value, unless the context clearly dictates otherwise.

Unless defined otherwise, all technical and scientific terms used herein have the same meaning as commonly understood by one of ordinary skill in the art to which this invention is related. The following terms are defined for purposes of the invention as described herein:

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" refers to an alkyl chain.

"Aryl" or "Ar" refers to a monovalent aromatic carbocyclic group of from 5 to 14 carbon atoms having a single ring (e.g., benzo) or multiple condensed rings (e.g., naphthyl or anthryl) which condensed rings may or may not be aromatic provided that the point of attachment is at an aromatic carbon atom.

"Heteroaryl" refers to an aromatic group of from 1 to 10 carbon atoms and 1 to 4 heteroatoms (e.g., oxygen or nitrogen) within the ring.

"Heterocycle" or "heterocyclic" refers to a saturated or unsaturated group having a single ring or multiple condensed rings, including fused bridged and spiro ring systems, from 1 to 10 carbon atoms and from 1 to 4 hetero atoms (e.g., nitrogen or oxygen) within the ring wherein, in fused ring systems, one or more the rings can be cycloalkyl, aryl or heteroaryl provided that the point of attachment is through the non-aromatic ring.

"Salt" refers to acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, trifluoroacetate, maleate, oxalate, and the like.

The term "dye" as used herein refers to a compound that emits light to produce an observable detectable signal.

The present invention relates to actinomycin-based fluorescent compounds. The subject compounds can be excited by light having a wavelength of about 450-600 nm and emit radiation in the near IR region of the electromagnetic spectrum (e.g., about 600-800 nm) and are represented by the chemical structure of Formula 1:

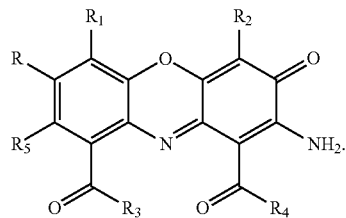

Formula 1

The substituents $R_1$, $R_2$, $R_3$, and $R_4$, are independently a moiety comprising 1-30 atoms selected from H, O, C, and N. $R_1$, $R_2$, $R_3$, and/or $R_4$, may have linear, branched, or cyclic configuration and may independently include aliphatic and/or aromatic moieties. Substituent R is H or $NH_2$. $R_5$ is H or a halogen (e.g., F, Cl, or Br).

Substituents $R_1$ and $R_2$ of Formula 1 can be alkyl groups, which may be the same or different. The alkyl group(s) can have between 1 to 10 carbon atoms. In certain embodiments, the alkyl group has less than 5 carbon atoms. In yet other embodiments, the alkyl group is ethyl or methyl. In certain embodiment, the alkyl group is methyl.

In certain embodiments, $R_3$ and $R_4$ of Formula 1 can be the same or different and can include a moiety such as —NHY, —NY, or —OY, where Y contains H, O, C, and/or N atoms. The atoms of Y can be arranged in a linear, branched, or cyclic configuration. Certain compounds include a substituent $R_3$ and/or $R_4$ that is —NHY. Compounds containing a relatively stable amide linkage may be less susceptible to hydrolysis or cleavage by an enzyme than those having more labile linkages (e.g., esters).

In other embodiments, $R_3$ or $R_4$ may have a structure —NY, such as —$NR_6$—$R_7$—$N(CH_3)_2$, wherein $R_6$ is H or an alkyl group having 1-6 carbons; $R_7$ is $(CH_2)_x$ or $[(CH_2)_2O]_y$; x=0-10 and y=0-10. In certain embodiments, $R_3$ and/or $R_4$ have a structure —O—$R_7$—$N(CH_3)_2$, wherein $R_7$ is $(CH_2)_x$ or $[(CH_2)_2O]_y$, and x=0-10 and y=0-10. In any of the embodiments described herein, $R_3$ and $R_4$ can be the same.

Compounds of Formula 1 may exist as an uncharged compound (e.g., free base) or as a charged compound (e.g., a positively charged compound). Representative compounds provided herein include those having the following chemical structures:

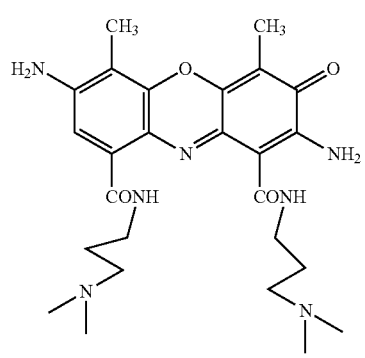

Formula 2

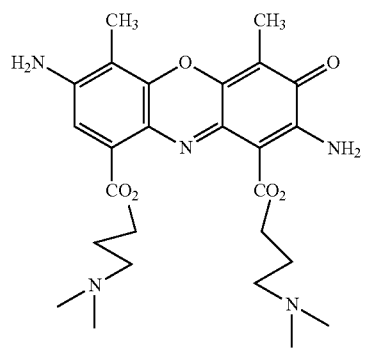

Formula 3

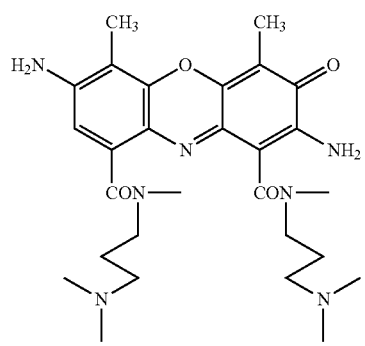

Formula 4

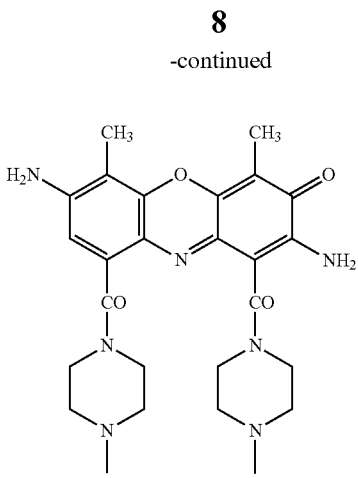

Formula 5

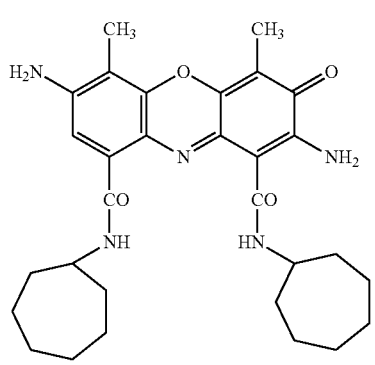

Formula 6

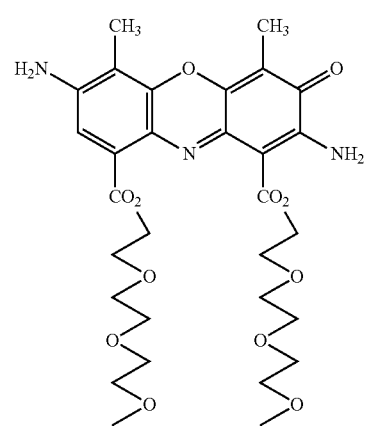

Formula 7

In certain embodiments, compounds having a chemical structure shown in Formula 1 exist in a salt form. For example, the compound may be a salt of a compound containing a quaternary nitrogen atom. In certain embodiments, the compound of Formula 1 may be a cation, and the salt may include a counterion, such as $OAc^-$, $I^-$, $Br^-$, $Cl^-$, $OTs^-$, $SO_4^{2-}$, $ClO_4^-$, tartrate, trifluoroacetate, or the like. Salts of the compounds described herein may be prepared using methods (e.g., counterion exchange using column chromatography techniques) that are well known to those skilled in the art (e.g., counterion exchange using column chromatography techniques).

Particular compounds may be prepared with quaternary nitrogen atom(s). Quaternization of nitrogen atoms may further enhance penetration of the compound through cell membranes of dead cells. For example, certain compounds include a substituent $R_3$ and/or $R_4$ (described above) that includes a quaternized nitrogen atom. For example, $R_3$ and/or $R_4$ can have a structure —$NR_6$—$R_7$—$N^+(CH_3)_3$, where substituent $R_6$ is H or an alkyl having 1-5 carbons; $R_7$ is $(CH_2)_x$ or $[(CH_2)_2O]_y$, x=0-5 and y=0-5. Other compounds have a substituent $R_3$ and/or $R_4$ with a structure —O—$R_7$—$N^+(CH_3)_3$, wherein $R_7$ is $(CH_2)_x$ or $[(CH_2)_2O]_y$; x=0-5 and y=0-5. Alternatively, $R_3$ and/or $R_4$ comprises a 3-7 membered ring formed of H, N, O, and/or C. $R_3$ or $R_4$ may have a structure —NH—Y, wherein Y is a cyclic or aliphatic group formed of 2-20 atoms selected from H, C, N, and O. Y may include an alicyclic or heterocyclic moiety. In any of the embodiments described herein, $R_3$ and $R_4$ can be the same.

Representative compounds with quaternary nitrogen atoms include those having the following chemical structures:

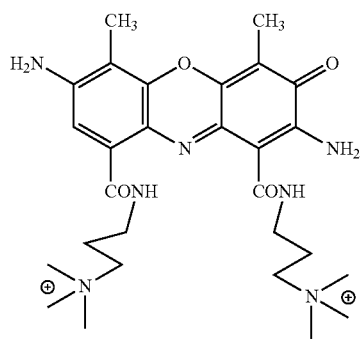

Formula 8

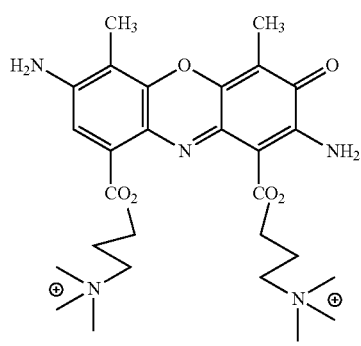

Formula 9

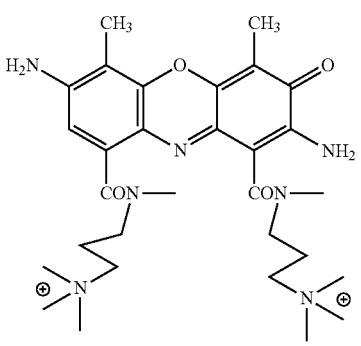

Formula 10

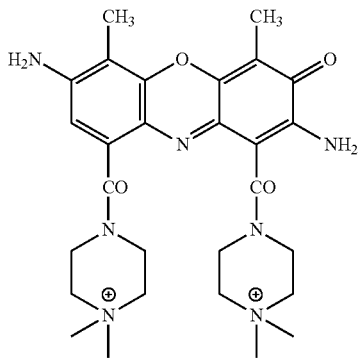

Formula 11

The compounds of the invention are soluble in biologically compatible solvents, such as water, buffers, DMSO, or DMF, which allows for easy sample preparation for fluorescence-based assays.

Applications and Methods of Use

The compounds provided herein may be used in various fluorescence-based technologies and assays. The compounds of the invention may be used to directly stain or label a sample so that the sample can be identified or quantitated. For example, such compounds may be added as part of an assay for a biological target analyte or as a detectable tracer element in a biological or non-biological fluid.

Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biofilms, and the like. The cells may also be adhered to a surface, such as to plastic or glass plates, coverslips, or other surfaces.

Alternatively, the sample is a solid. For example, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids, or from a biological solid tissue sample which has been dissociated. Alternatively, the sample is obtained from an environmental source such as soil, water, or air; or from an industrial source such as taken from a waste stream, a water source, a supply line, or a production lot.

In yet another embodiment, the sample is present on or in solid or semi-solid matrix. The matrix may be a membrane or microsphere. Alternatively, the matrix may be an electrophoretic gel, such as is used for separating and characterizing nucleic acids or proteins, or a blot prepared by transfer from an electrophoretic gel to a membrane. The matrix may be a silicon chip or glass slide, and the analyte of interest has been immobilized on the chip or slide in an array (e.g. the sample comprises proteins or nucleic acid polymers in a microarray). Alternatively, the sample may be present in a solvent (e.g., organic solvent). In some embodiments, the matrix is a microwell plate or microfluidic chip, and the sample is analyzed by automated methods, typically by various methods of high-throughput screening, such as drug screening.

The present compounds generally may be combined with a sample of interest under conditions selected to yield a detectable optical response. The compound typically associates in a non-covalent manner to form a complex with an element of the sample, or is simply present within the bounds of the sample or portion of the sample. The sample is then illuminated at a wavelength selected to elicit the optical response. Typically, staining the sample is used to determine a specified characteristic of the sample by further comparing the optical response with a standard or expected response.

A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

For biological applications, the compounds of the invention are typically used in an aqueous, mostly aqueous or aqueous-miscible solution prepared according to methods generally known in the art. The exact concentration of dye compound is dependent upon the experimental conditions and the desired results, but typically ranges from about one nanomolar to one millimolar or more. The optimal concentration is determined by systematic variation until satisfactory results with minimal background fluorescence are accomplished.

The compounds are advantageously used to stain samples with biological components. The sample may comprise heterogeneous mixtures of components (including intact cells, cell extracts, bacteria, viruses, organelles, and mixtures thereof), or a single component or homogeneous group of components (e.g. natural or synthetic amino acid, nucleic acid or carbohydrate polymers, or lipid membrane complexes). The described compounds are generally non-toxic to living cells and other biological components, within the concentrations of use.

The compound is combined with the sample in any way that facilitates contact between the compound and the sample components of interest. Typically, the dye compound or a solution containing the compound is simply added to the sample. Certain compounds of the invention tend not to be permeant to membranes of living biological cells. However, the ability of the present compounds to rapidly and effectively enter cells with compromised cell membranes (e.g., dead cells or fixed cells) enables their use in cellular analysis assays.

The actinomycin analogues of the invention have been modified to minimize the size of substituents on the molecule, thus making them more permeable to cell membranes than other actinomycin-based compounds, such as 7-AAD, which include larger substituents (e.g., cyclic peptides). Modified actinomycins of the invention are capable of rapidly and efficiently penetrating cell membranes. Dead cells incubated in a solution of a compound, as described herein (at concentrations typically used in cellular analysis assays), typically will be stained within about 5 to about 15 minutes. Staining of dead cells also may be achieved in shorter times (e.g., less than 5 minutes), depending on the type and condition of the cells.

Optionally, the sample is not washed after staining. The sample is optionally combined with one or more other solutions in the course of staining, including wash solutions, permeabilization and/or fixation solutions, and solutions containing additional detection reagents. An additional detection reagent typically produces a detectable response due to the presence of a specific cell component, intracellular substance, or cellular condition, according to methods generally known in the art. Where the additional detection reagent has, or yields a product with, spectral properties that differ from those of the subject dye compounds, multi-color applications are possible. This is particularly useful where the additional detection reagent is a dye or dye-conjugate having spectral properties that are detectably distinct from those of the staining dye.

At any time after or during staining, the sample is illuminated with a wavelength of light selected to give a detectable optical response, and observed with a means for detecting the optical response. Equipment for illuminating the dye compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors. Preferred embodiments of the invention are dyes that are be excitable at or near the wavelengths 450-600 nm, as these regions closely match the output of standard equipment.

The optical response is optionally detected by visual inspection or by use of a device, such as, for example, CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is evaluated using a flow cytometer, examination of the sample optionally includes sorting portions of the sample according to their fluorescence response.

In one aspect, a method of determining whether a nucleic acid molecule is present in a sample is provided that involves contacting a sample with a compound of the invention. The presence of absence of a detectable optical response under the desired conditions will be indicative of the presence or absence of nucleic acid molecules in the sample.

In another aspect, a method of staining a sample containing nucleic acid molecules is provided in which a sample is contacted with a compound, as described herein. An exemplary method involves combining a solution that contains a compound of the invention with a sample in a concentration sufficient to yield a detectable optical response under the desired conditions. Under the appropriate conditions, the actinomycin-based compound can form a complex with nucleic acid (e.g., DNA) present in the sample, which generates a detectable optical response under the desired conditions.

In certain embodiments, the sample is a biological sample. The biological sample can include live cells, fixed cells, or fixed and permeabilized cells, or free cell nuclei. The cells may be treated with a cell fixative reagent, a cell permeabilizing reagent, or a combination of a cell fixative reagent and cell permeabilizing reagent. The compounds of the invention may be used for treating samples containing mixtures of living cells (cells with intact membranes) and dead cells (cells with compromised cell membranes) for the purposes of identifying dead cells or distinguishing the dead cells from the live cells, and for treating samples containing fixed cells for the purpose of measuring DNA content. The sample may include nucleic acid molecules, proteins, nucleotides, nucleosides, or any other biological material.

As discussed above, the described compounds have an affinity for nucleic acid molecules and can form a complex with such molecules, which can be detected optically. The complex can form between a nucleic acid molecule and any compound of the invention. Typically, the compound is non-covalently associated with the nucleic acid molecule. The nucleic acid molecule may be from any source and may be a nucleic acid polymer, such as, DNA or RNA. In certain embodiments, the described compounds can form a complex with double-stranded DNA. In other embodiments, the described compounds can form a complex with double-stranded RNA. Alternatively, the nucleic acid molecule may be an oligonucleotide (e.g., DNA oligonucleotide). Compounds of the invention typically have a higher affinity for double-stranded DNA molecule over double-stranded RNA molecules.

The nucleic acid molecule may be present in any type of biological sample. For example, the nucleic acid molecule may be present in a sample that includes live cells, fixed cells, eukaryotic cells, prokaryotic cells, biological fluids, isolated cell nuclei, or tissue. The sample may contain dead cells or the isolated nuclei of cells. The nucleic acid molecule may be present in the nucleus of a eukaryote or a prokaryote. The nucleic acid molecule may be contained within the cell (e.g., the nucleus of a cell) or may be a chromosome or a chromosomal fragment.

The compounds of the invention are particularly useful for staining cells with compromised cell membranes. Such cells include dead cells and fixed cells, where the dead or fixed cells contain nucleic acid molecules (e.g., DNA). The cells may be untreated or treated with a cell fixative reagent or cell permeabilizing reagent or a combination of a cell fixative reagent and a cell permeabilizing reagent. In certain embodiments, biological sample contains dead or fixed cells (e.g., eukaryotes), and the nucleic acid molecules are contained within the dead or fixed cells.

The nucleic acid molecules may be present in an aqueous solution (e.g., a buffer or biological fluid) that may or may not include cellular material. Alternatively, the complex may be present in a polymeric gel or in an electrophoretic matrix or in a solvent, such as an organic solvent (e.g., DMSO, DMF, alcohol, or the like) or water.

Prior to association with a nucleic acid molecule, the compounds of the invention exhibit little or no fluorescence. Once the compound complexes with a nucleic acid molecule, the dye becomes fluorescent and may be optically detected. The ratio of compound:nucleic acid molecule that elicits an optical response may be determined empirically, but typically nanomolar to micromolar or more of compound is used to produce a detectable optical signal. The optimal concentration is determined by systematic variation until satisfactory results with minimal background fluorescence are accomplished. In one embodiment, the compound may be used at a concentration of 1 nM to about 500 nM. In other embodiments, the compound may be used at a concentration of about 500 nM to about 1 µM. In yet other embodiments, the compound may be used at a concentration of about 1 µM to about 10 µM. In yet other embodiments, the compound may be used at a concentration of about 10 µM to about 100 µM. In yet other embodiments, the compound may be used at a concentration of about 100 µM to about 1 mM.

The fluorescence properties of the described compounds, by virtue of their relatively long emission wavelengths, make the compounds particularly useful in multiplex applications with fluorophores that emit in the UV or visible portion of the spectrum. For example, the disclosed compounds may be used in multiplex assays in combination with multiple fluorophores and using several types of lasers and other excitation sources (e.g., mercury arc lamps, diodes, and other focused light sources).

Provided herein are methods for detecting the presence of a nucleic acid molecule in a sample and methods for staining a biological sample containing nucleic acid. A biological sample may be contacted with any compound according to the invention. A representative method for detecting the presence of nucleic acid molecules in a sample involves preparing a mixture of a compound according to the invention and a sample. The sample may be a biological sample containing a plurality of nucleic acid molecules. The mixture is incubated for a sufficient amount of time for the compound to associate with the nucleic acid molecule in the sample; to form a complex. After sufficient time for the compound to complex with nucleic acids in the sample, the sample is excited with a light source (e.g., a laser). Due to its optical properties, the compound can emit a fluorescence signal upon excitation. Preferably, the light source provides photons of a wavelength that fall within the absorption wavelength range of the compound (e.g., 400-700 nm). For certain compounds the light source used provides photons having a wavelength of less than 700 nm (e.g., about 450-600 nm).

Compounds of the invention typically emit light in the IR region of the electromagnetic spectrum and more typically in the near IR region of the spectrum.

Depending on the assay, it may be desirable to also quantify the amount of nucleic acid present in the sample. Methods are provided for detecting the presence of nucleic acids in a sample including quantification of the nucleic acid detected. Exemplary methods for quantifying nucleic acid content in cells involve combining a compound according to the invention with a sample that includes cells, which contain nucleic acid molecules, to form a mixture. The mixture is incubated for a sufficient amount of time for the compound to penetrate into the cells. The incubated mixture is illuminated with an appropriate wavelength to generate a detectable optical response. Illumination may be achieved by the use of an excitation laser, laser diode, or mercury arc lamp or other such focused light source. The optical response can be detected to determine presence of nucleic acid molecules in the sample. Detection may be achieved using instrumentation and methods well known to those skilled in the art, such as, for example, flow cytometry, confocal laser scanning microscopy, and imaging (e.g., high content image analysis). Methods of quantifying nucleic acid content in cells using fluorophores are well known to those skilled in the art and include, for example, flow cytometry or imaging the biological sample. Exemplary detection equipment includes imaging-based flow cytometers, slide-based imaging cytometers, and high content imaging systems.

The compounds of the invention are also able to penetrate the cell membrane of live cells. The unique fluorescence properties and ability of the compounds of the invention to enter viable cells make these compounds appropriate for use in cell cycle analysis studies. Other applications include the use of flow cytometry to differentiate cells in various stages of the cycle or to differentiate between living and dying or dead cells.

In another aspect, detection of nucleic acid molecules in a sample may be accomplished using imaging. The compound is combined with a sample (e.g., a biological fluid or a sample of cells) that contains nucleic acid molecules (e.g., DNA) to form a mixture. The solution is incubated for a sufficient amount of time for the compound to associate with the nucleic acid in the sample (e.g., about 5 minutes to about 15 minutes or to one hour or more). In certain embodiments, the solution is incubated for 5 minutes or less. The incubated sample is then illuminated with an appropriate wavelength of light to generate a detectable optical response resulting from the presence of a complex of the compound with a nucleic acid molecule in the sample. Illumination may be achieved by the use of an excitation laser, laser diode, or mercury arc lamp or other such focused light source. The optical response can be detected to determine presence of nucleic acid molecules in the sample. Detection may be achieved by imaging to determine the presence and location of nucleic acid molecules in a sample.

In yet another aspect, methods for evaluating the viability of cells in a sample are provided. The methods involve combining a compound according to the invention with a sample to form a mixture. The sample contains a plurality of cells that contain nucleic acid molecules. The mixture is incubated for a sufficient amount of time for the compound to associate with the nucleic acid molecule in the sample. The incubated sample is illuminated with an appropriate wavelength to generate a detectable optical response. Detection of the illuminated sample provides information about the viability of the cells in the sample.

The compounds of the invention may be incorporated into kits that facilitate the practice of various assays (e.g., detecting nucleic acid molecules in a sample). An exemplary kit includes a compound according to the invention. The compound may be in a dry form or may be dissolved in a diluent (e.g., a buffer or organic solvent). Additional components may be included in the kit, such as sample preparation reagents, buffering agents, organic solvents, dyes, solvents, fixatives, permeabilizing agents, RNase, reaction components to carry out coupling reactions (e.g., dye-azide conjugates, CuSO4, and ascorbate), microspheres, fixed cells or fixed nuclei. Kits of the invention also may include instructions for carrying out an assay, describing use of kits in the methods described herein.

The following examples are given for the purpose of illustrating the invention and shall not be construed as being a limitation on the scope of the invention or claims.

EXAMPLES

Example 1

Synthesis of Compound 1

A mixture of 10 g of 3-hydroxy-4-methyl-2-nitrobenzoic acid, 22 g of benzyl bromide, and 28 g of $K_2CO_3$ in 100 mL of DMF was heated at 85° C. overnight. After the reaction mixture was cooled to room temperature, it was diluted with ethyl acetate, washed with water, and dried over anhydrous $Na_2SO_4$ to obtain crude product 1 (22 g) as sticky light yellow oil. MS ($ESI^+$) [m/z]: 376 $[M]^+$.

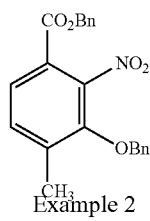

Example 2

Synthesis of Compound 2

To 22 g of compound 1 in 200 mL of MeOH, 10% NaOH (150 mL) was added. The mixture was heated at 100° C. for 3 h and then cooled to room temperature. MeOH was removed under reduced pressure and the residue was acidified with conc. HCl and the precipitate was collected by filtration and dried under vacuum to give white, solid product 2 (13.85 g). MS ($ESI^+$) [m/z]: 286 $[M]^+$.

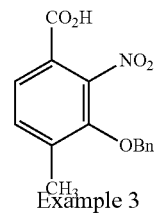

Example 3

Synthesis of Compound 3

To 8.3 g of compound 2 in 100 mL of dry $CH_2Cl_2$ at 0° C., 5 mL of oxalyl chloride was added slowly and the mixture was stirred at room temperature for 4 hours. All volatile components were removed under reduced pressure. The residue was redissolved in 100 mL of dry $CH_2Cl_2$ and 5.4 mL of 3-(dimethylamino)-1-propylamine was added slowly at room temperature and after stirring for 1 hour, the volatile components was removed under reduced pressure, 100 mL of water was added the product was extracted with EtOAc. The organic layer was dried over anhydrous $Na_2SO_4$ to obtain 3 (11.5 g) as light yellow and sticky oil. MS ($ESI^+$) [m/z]: 370 $[M]^+$.

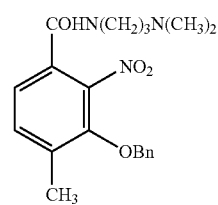

Example 4

Synthesis of Compound 4

To 5.6 g of compound 3 in 100 mL of MeOH in a hydrogenation bottle, 1.5 g of 10% Pd/carbon was added, and the mixture was subjected to hydrogenation at 35 psi for 3 h. Pd catalyst was filtered through celite and to the filtrate solution, 15 g of potassium ferricyanide (III) in 400 mL of PBS buffer (pH 7) was added and the mixture was stirred at room temperature for 30 min. The precipitate was collected by filtration and dried under vacuum to give product 4 (11.46 g) as a red solid. MS ($ESI^+$) [m/z]: 495 $[M]^+$.

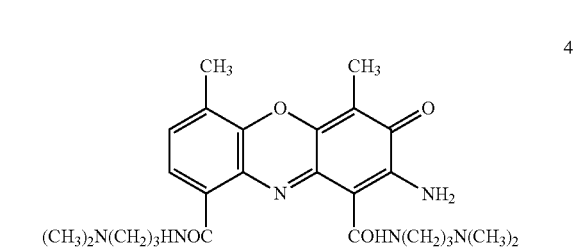

Example 5

Synthesis of Compound 5

To 960 mg of compound 4 in 10 mL of conc. $H_2SO_4$ at 0° C., 210 mg of 90% fuming nitric acid in 3 mL of conc. $H_2SO_4$ was added slowly. The mixture was stirred at the cold temperature for 30 min and the reaction mixture was poured onto ice, basified with solid Na$_2$CO$_3$ and extracted with n-BuOH. The organic extract was dried over anhydrous Na$_2$SO$_4$ to give product 5 (640 mg) as dark solid. MS (ESI$^+$) [m/z]: 540 [M]$^+$.

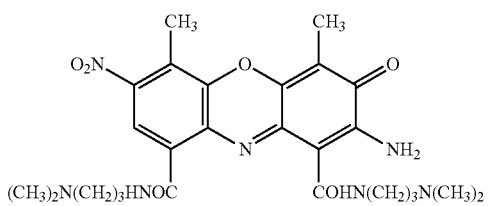

5

Example 6

Synthesis of Compound 6

To 630 mg of crude compound 5 in 30 mL of CHCl$_3$ in a hydrogenation bottle 100 mL of MeOH was added followed by 400 mg of 10% Pd on carbon and the mixture was then subjected to hydrogenation at 35 psi for 4 h. The Pd catalyst was filtered through a celite pad and the filtrate was stirred at room temperature for 3 h with air bubbling through the solution for the entire period. Removal of volatile components under reduced pressure yielded 6 (540 mg) as dark purple solid. MS (ESI$^+$) [m/z]: 510 [M]$^+$.

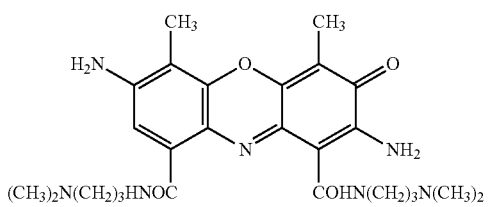

6

Example 7

Synthesis of Compound 7

To a 100 mg of crude compound 6 in DMF (15 mL) at room temperature, iodomethane (0.5 mL) was added and the resulting mixture was stirred for 30 min. All volatile components were removed under reduced pressure and the residue was purified by HPLC to give compound 7 (66 mg) as dark purple solid. MS (ESI$^+$) [m/z]: 540 [M]$^+$.

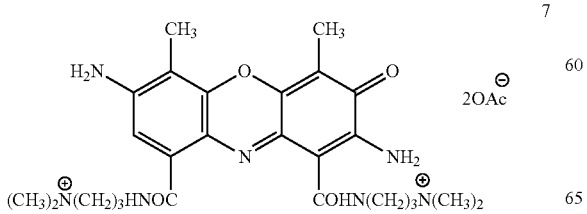

7

Example 8

Synthesis of Compound 8

Compound 8 was prepared, starting from compound 2 and 3-(dimethylamino)-1-propyl alcohol, by following the same procedures for the transformation of compound 2 to compound 7. MS (ESI$^+$) [m/z]: 512 [M]$^+$.

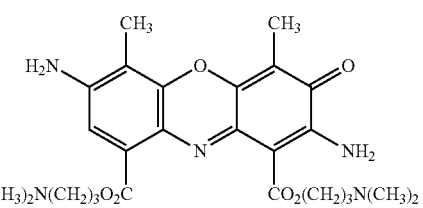

8

Example 9

Synthesis of Compound 9

Compound 9 was prepared from the reaction of compound 8 and iodomethane. MS (ESI$^+$) [m/z]: 542 [M]$^+$.

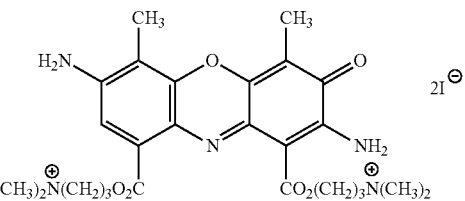

9

Example 10

Synthesis of Compound 10

Compound 10 was prepared from compound 2 and N,N,N'-trimethylpropanediamine by following the aforementioned procedures. MS (ESI$^+$) [m/z]: 538 [M]$^+$.

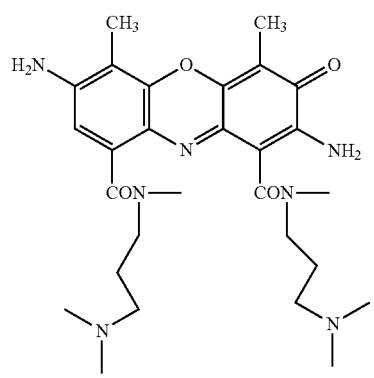

10

Example 11

Synthesis of Compound 11

Compound 11 was prepared from reaction of compound 10 and iodomethane. MS (ESI⁺) [m/z]: 568 [M]⁺.

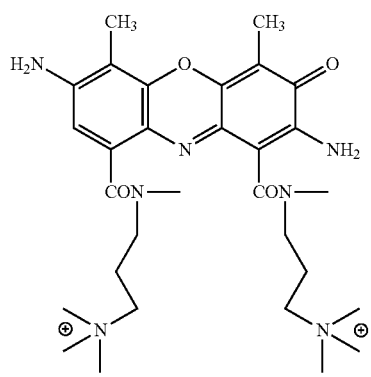

11

Example 12

Synthesis of Compound 12

Compound 12 was prepared from compound 2 and 1-methylpiperazine by following the aforementioned procedures. MS (ESI⁺) [m/z]: 506 [M]⁺.

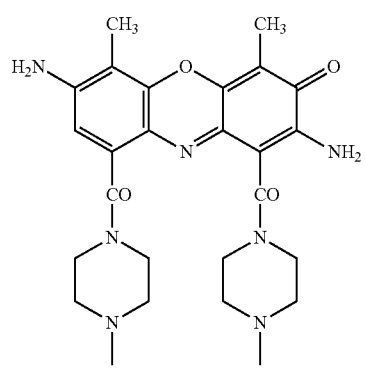

12

Example 13

Synthesis of Compound 13

Compound 13 was prepared from reaction of compound 12 and iodomethane. MS (ESI⁺) [m/z]: 536 [M]⁺.

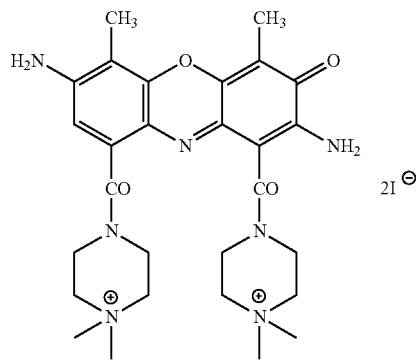

13

Example 14

Synthesis of Compound 14

Compound 14 was prepared from compound 2 and cycloheptylamine by following the aforementioned procedures. MS (ESI⁺) [m/z]: 532 [M]⁺.

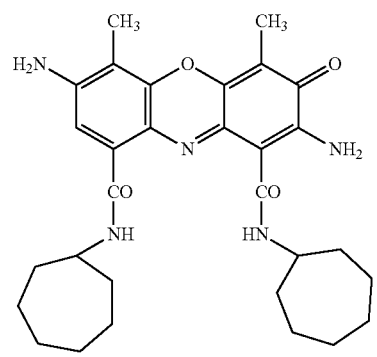

14

Example 15

Synthesis of Compound 15

Compound 15 was prepared from compound 2 and tri(ethylene glycol) monomethyl ether by following the aforementioned procedures. MS (ESI⁺) [m/z]: 634 [M]⁺.

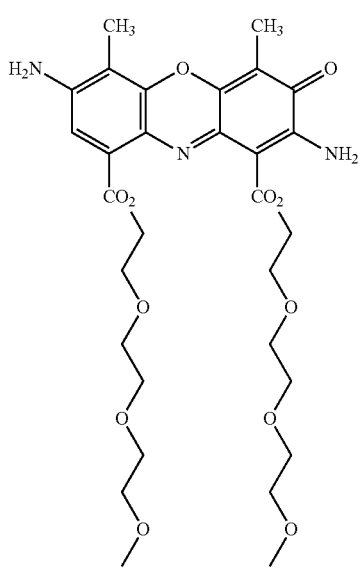

Example 16

Analysis of Stained T-Cell Leukemia Cells

Differentiation between live and dead cells is determined by measuring the ratio between the fluorescence emitted by live and dead cells using flow cytometry. The ratio of fluorescence emitted by treated living and dead cells, as measured by flow cytometry, is generally ≥40 (Dead:Live). A lower ratio may still result in clear separation of live and dead cells. The compounds entered cells with compromised membranes (dead cells), whereas living cells with an intact cell membrane excluded the dye from entering the cell.

A mixture 50:50 of live and heat-killed Jurkat T lymphocytic leukemia cells are suspended in phosphate buffered saline (PBS) at 1×10$^6$/ml Compound 7 is added to the cells at final concentration of 1 µM, and incubated for 5 minutes at room temperature. Cells are run through a Becton Dickinson (BD) LSRII Flow Cytometer using 670/14 bandpass (BP) with 488 nm excitation. Analysis was done using BD FASCDiva software. Live cells are identified with the marker P1. Dead cells are identified with the marker P2. The ratio of median fluorescence intensity (MFI) of dead:live cells is 105 (FIG. 1), indicating distinct separation of live and dead cells.

Example 17

Flow Cytometry Analysis of Stained Chinese Hamster Ovary Cells

Figure 2:
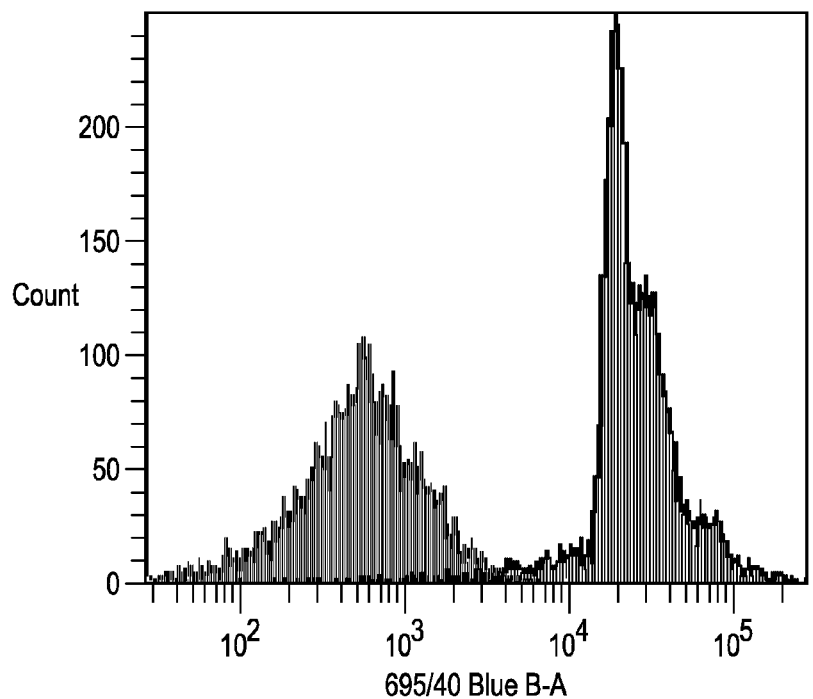
FIG. 2 is a flow cytometry plot for a mixture (50:50) of live and heat-killed CHO-M1 cells treated with 1 µM Compound 7 and incubated for 5 minutes at room temperature. Live cells are identified in curve on left, and dead cells are identified in curve on right. The live and dead cells are distinctly separated.

CHO-M1 Chinese hamster ovary cells were harvested by trypsinization, washed with PBS. A mixture 50:50 of live and heat-killed CHO-M1 cells are suspended in PBS at 1×10$^6$/ml. Stain (Compound 7) is added to the cells at final concentration of 1 µM, and incubated for 5 minutes at room temperature. Cells are run through the Becton Dickinson (BD) LSRII Flow Cytometer using 695/40 bandpass (BP) with 488 nm excitation. Analysis was done using BD FASCDiva software. The histogram for the stained cells shows distinct separation of live and dead cells. The ratio of median fluorescence intensity (MFI) of Dead:Live cells of 45 (FIG. 2).

Example 18

Imaging Analysis of Stained Jurkat T-Leukemia Cells with Camptothecin Treatment

Figure 3:
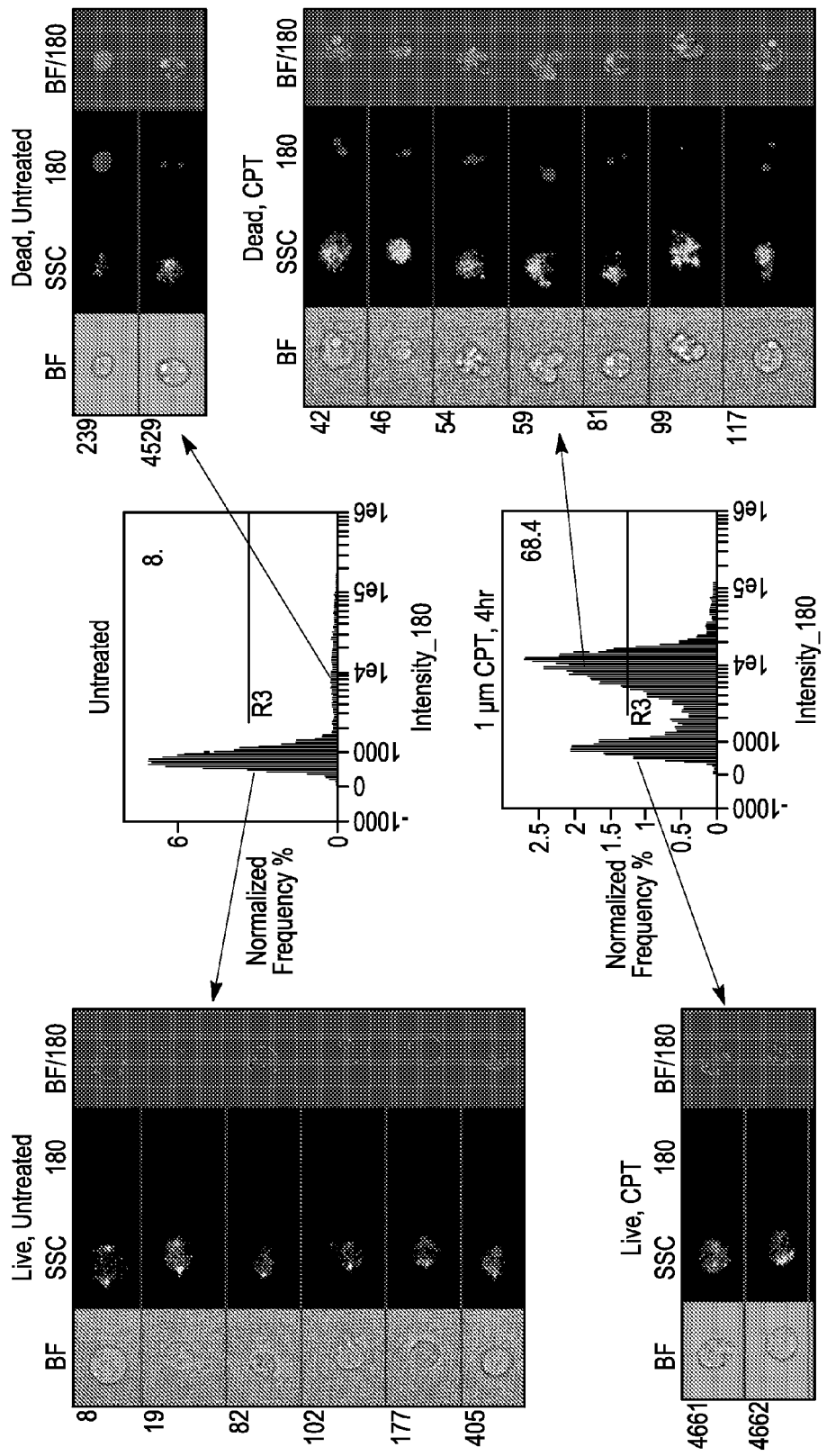
FIG. 3 shows brightfield images of Jurkat cells stained with Compound 7 for 15 minutes at room temperature, (untreated with camptothecin) (top middle) and treated with camptothecin (bottom middle).

Jurkat T cells were incubated in the presence or absence of 1 µM camptothecin (CPT) for 4 hours to induce apoptosis, then stained with 2.5 µM Compound 7 for 15 minutes at room temperature and analyzed on an AMNIS ImageStream multispectral imaging flow cytometer. Gating on 10,000 collected events with intermediate brightfield (BF) area and high BF aspect ratio (width:height) was performed to distinguish single cells from debris and multi-cellular clumps. Cells with nuclear dye uptake were gated (R3) on the Intensity 180 plot. Representative live and dead cell images are shown in FIG. 3. Cells untreated with camptothecin are shown in the top middle histogram of FIG. 3, with 8.0% stain positive (dead cells) as identified in the R3 gate. The positively stained cells show typical brightfield morphology of dead cells, while the cells negative (live cells) show typical brightfield morphology of live cells.

Cells treated with the apoptotic inducing agent camptothecin (FIG. 3B) (bottom middle histogram), with 68.4% stain positive as identified in the R3 gate. The positively stained cells show typical brightfield morphology of dead cells and stained nuclei typical of apoptosis and cell death that is condensed and fragmented, while the cells negative for staining (live cells) show typical brightfield morphology of live cells. The brightfield image data shows that camptothecin induced significant cell death measurable by staining with Compound 7 nucleic acid stain, and the images of cells labeled positive for stain show condensed and fragmented nuclei characteristic of apoptosis and cell death. Cells negative for stain show morphology typical of healthy cells.

Example 19

Imaging Analysis of Stained HeLa Cells with Valinomycin Treatment

Figure 4:
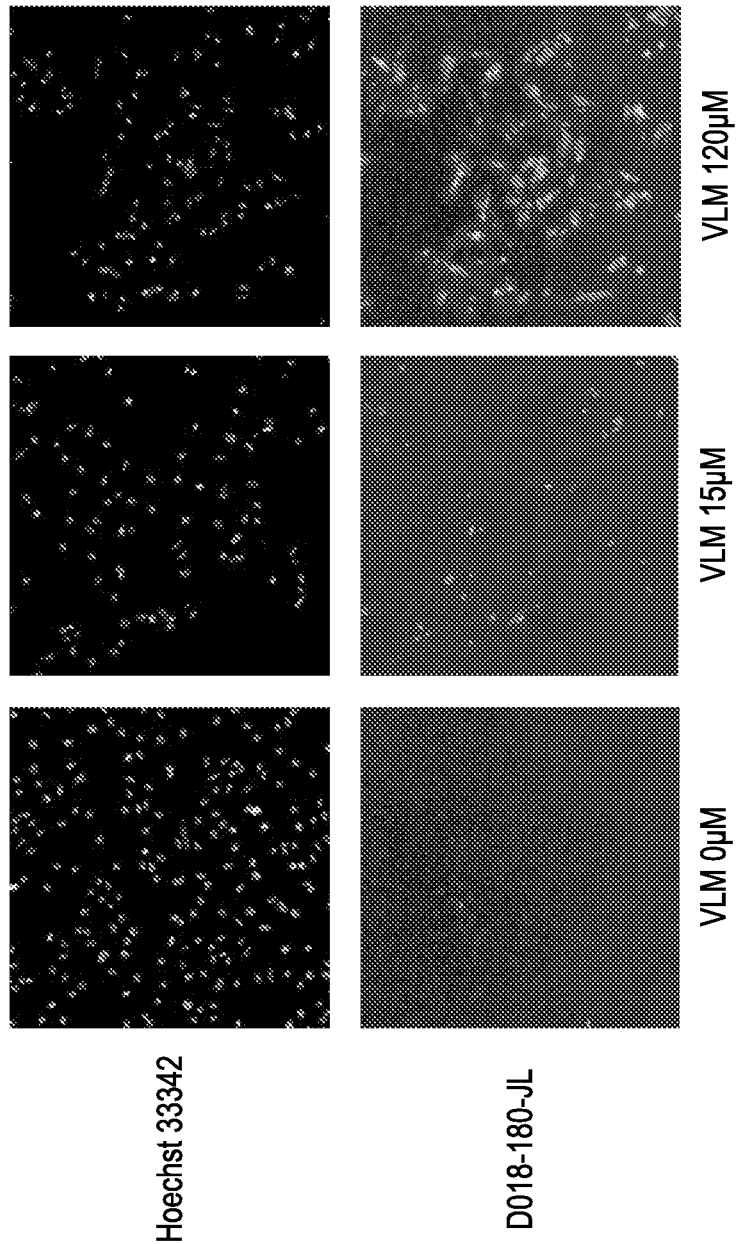
FIG. 4 shows images of HeLa cells (untreated or treated with 15 µM or 120 µM valinomycin as a cellular killing agent). After 24 hour treatment, cells were labeled with 1 µM Compound 7 for 30 minutes at 37° C. to label dead cells and with Hoechst 33342 as a nuclear counterstain. Hoechst 33342 identifies all cells with each treatment, labeling both live and dead cells. Only cells treated with valinomycin stain positively with Compound 7 stain. The number of dead cells increases with the concentration of valinomycin.

HeLa cells were either untreated or treated with two concentrations (15 µM and 120 µM) of valinomycin (VLM) as a killing agent for 24 hours before labeling with Compound 7 and with the nuclear counterstain Hoechst 33342 dye (Invitrogen Corporation, Carlsbad, Calif.). At 24 hours of treatment, normal cell growth medium containing 2× final concentration of Hoechst 33342 and Compound 7 was added to the existing medium to result in 1× final concentration. Cells were incubated for 30 minutes at 37° C. and then the drug/dye mixture was replaced with PBS for imaging using a high content automated imaging system (ArrayScan VTI from Thermo/Fisher) using a Texas Red filter set. Most of the cells treated with 120 µM valinomycin showed staining with Compound 7, indicating this concentration of valinomycin is effective in killing HeLa cell, while in only a portion of the cells treated with lower valinomycin concentration (15 uM) show staining with Compound 7 indicating this concentration of valinomycin is less effective in killing HeLa cells. The majority of control cells (not treated with valinomycin) show no staining of Compound 7 stain (FIG. 4).

Example 20

Flow Cytometry DNA Content Analysis of Fixed HL60 Cells

Flow cytometry is used to measure DNA content in labeled fixed; fixed and permeabilized cells; and free nuclei. The DNA content measurements provide values for % CV and linearity. The % CV of normal diploid cells in a flow cytometry histogram is typically ≤8%. The % CV of a tumor may be higher due to the presence of multiple tumor subpopulations. However, tumor CVs of ≤8% are recommended for useful S-Phase determinations (*Cytometry*. 1993, Vol. 14 (5), page 474). Linearity is the observed ratio between the DNA Diploid G2M and G0G1 positions. Typically, this value is about two. Under normal circumstances, however, linearity can deviate from this ideal value. (see, MODFIT LT user guide, June 2000).

HL60 cells were fixed with cold 70% alcohol and stored at −20° C. overnight, washed and then suspended in 0.1% TRITON X with 1% bovine serum albumin (BSA) in PBS at $1\times10^6$/ml. Cells were stained with 1 µM Compound 7 with the addition of RNase, and incubated for 30 minutes at room temperature. Cells are run through the Becton Dickinson (BD) LSRII Flow Cytometer using 695/40 bandpass (BP) with 488 nm excitation. Analysis was done using BD FASCDiva software. Cell modeling was performed with Verity House MODFIT LT analysis software. This compound demonstrates staining for DNA content cell cycle. Typical DNA content cell cycle histogram shows G0G1 phase, S phase, and G2M phase. Further analysis using MODFIT Software shows that the compound stains live cells for DNA cell cycle where the % CV of G1-phase ≤8%, and the observed ratio indicates linearity of staining. Analysis of the cell cycle histogram gives % CV of G1-phase 5.43% and G2/G1 ratio is 2.02, results within the limits of the cell cycle model.

Example 21

Flow Cytometry DNA Content Analysis of Fixed Jurkat Cells

Jurkat cells were fixed with 4% paraformaldehyde in PBS for 15 minutes washed and then suspended in 0.1% TRITON X with 1% BSA in PBS at $1\times10^6$/ml. Cells were stained with 1 µM Compound 7 with the addition of RNase, and incubated for 30 minutes at room temperature. Cells are run through a Becton Dickinson (BD) LSRII Flow Cytometer using 695/40 bandpass (BP) with 488 nm excitation. Analysis was done using BD FASCDiva software and cell modeling was also performed with Verity House MODFIT LT analysis software. This compound demonstrates staining for DNA content cell cycle. Typical DNA content cell cycle histogram is demonstrated showing G0G1 phase, S phase, and G2M phase, as obtained on the live cell gate.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound having the structure:

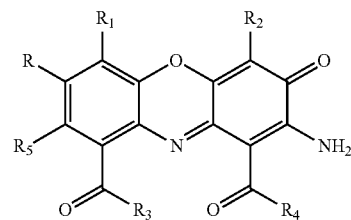

wherein R is H or $NH_2$;

$R_3$ and/or $R_4$ comprise a quaternary nitrogen atom wherein $R_3$ and/or $R_4$ has a structure —$NR_6$—$R_7$—$N^+(CH_3)_3$, wherein $R_6$ is H or an alkyl having 1-5 carbons; $R_7$ is $(CH_2)_x$ or $[(CH_2)_2O]_y$; x=0-5; and y=0-5; $R_3$ and/or $R_4$ has a structure —O—$R_7$—$N^+(CH_3)_3$, wherein $R_7$ is $(CH_2)_x$ or $[(CH_2)_2O]_y$; x=0-5; and y=0-5; $R_3$ and/or $R_4$ includes a 3-7 membered ring formed of H, N, O and/or C; or $R_3$ and/or $R_4$ comprise —NHY, —NY, or —OY, wherein Y comprises H, O, C, N or a combination thereof, wherein the atoms are in a linear, branched, or cyclic configuration;

$R_1$ and $R_2$ are independently alkyl groups having 1 to 10 carbon atoms; and $R_5$ is H, F, or Cl.

2. The compound of claim 1, further comprising a counterion selected from the group consisting of $OAc^-$, $I^-$, Br, Cl, OTs, $SO_4^{-2}$, $ClO_4^-$, tartrate, and trifluoroacetate.

3. The compound of claim 1 wherein the alkyl group of $R_1$ and $R_2$ is methyl.

4. The compound of claim 1 wherein $R_5$ is hydrogen.

5. The compound of claim 1 having the structure:

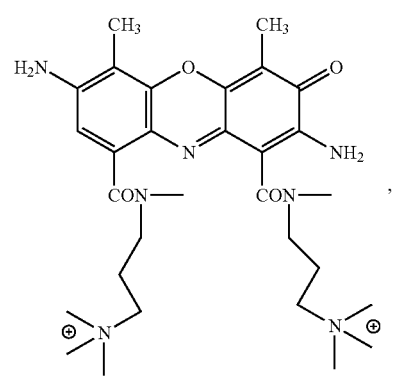

25
-continued

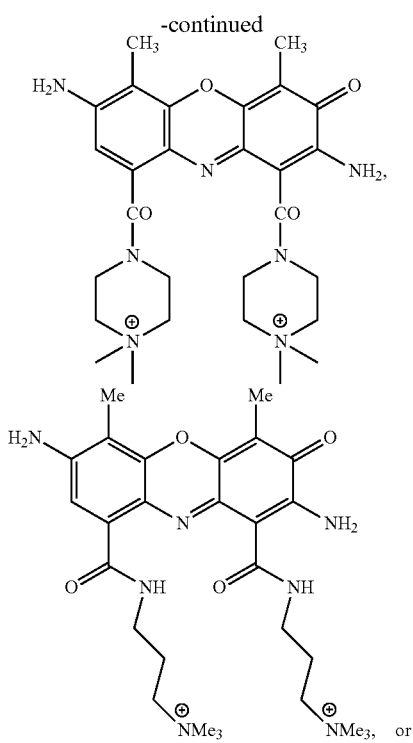

26
-continued

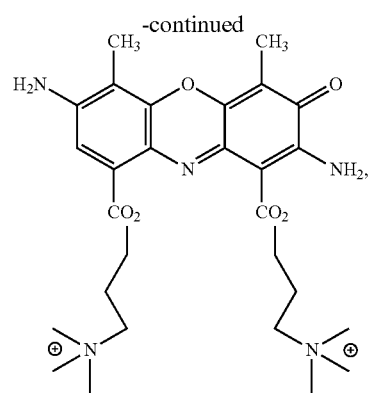

or a salt thereof.

6. The compound of claim 1, $R_3$ or $R_4$ includes a 3-7 member ring formed of H, N, O, and/or C.

7. The compound of claim 1, wherein $R_3$ or $R_4$ has a structure —$NR_6$—$R_7$—$N^+(CH_3)_3$, wherein $R_6$ is H or an alkyl having 1-5 carbons; $R_7$ is $(CH_2)_x$ or $[(CH_2)_2O]_y$; x=0-5; and y=0-5.

8. The compound of claim 1, wherein $R_3$ or $R_4$ has a structure —O—$R_7$—$N^+(CH_3)_3$, wherein $R_7$ is $(CH_2)_x$ or $[(CH_2)_2O]_y$; x=0-5; and y=0-5.

* * * * *